United States Patent
DiFrancesco

(10) Patent No.: US 7,407,503 B2
(45) Date of Patent: Aug. 5, 2008

(54) MEDICAL-TREATMENT ELECTRODE ASSEMBLY HAVING TREATMENT-MONITORING APPLICATION

(75) Inventor: Mark DiFrancesco, Loveland, OH (US)

(73) Assignee: Ethicon Endo-Surgey, Inc., Cincinnati, OH (US)

( * ) Notice: Subject to any disclaimer, the term of this patent is extended or adjusted under 35 U.S.C. 154(b) by 609 days.

(21) Appl. No.: 11/017,893

(22) Filed: Dec. 21, 2004

(65) Prior Publication Data

US 2006/0136029 A1    Jun. 22, 2006

(51) Int. Cl.
*A61B 18/18* (2006.01)
*A61B 5/04* (2006.01)

(52) U.S. Cl. .......................................... 606/41; 600/372

(58) Field of Classification Search ............. 606/27–31, 606/41, 42, 45–50; 607/101, 102, 1; 600/372, 600/374

See application file for complete search history.

(56) References Cited

U.S. PATENT DOCUMENTS

| | | | |
|---|---|---|---|
| 4,532,924 A * | 8/1985 | Auth et al. ..................... 606/50 |
| 4,765,331 A * | 8/1988 | Petruzzi et al. ................ 606/50 |
| 4,770,173 A * | 9/1988 | Feucht et al. ................ 607/152 |
| 4,836,214 A | 6/1989 | Sramek |
| 4,873,974 A * | 10/1989 | Hagen et al. ................... 606/39 |
| 5,109,870 A | 5/1992 | Silny et al. |
| 5,782,760 A * | 7/1998 | Schaer ........................ 600/381 |
| 5,916,213 A * | 6/1999 | Haissaguerre et al. ......... 606/41 |
| 6,290,699 B1 * | 9/2001 | Hall et al. ...................... 606/41 |
| 6,740,084 B2 * | 5/2004 | Ryan ............................ 606/41 |
| 6,922,579 B2 * | 7/2005 | Taimisto et al. ............. 600/374 |
| 2002/0120264 A1 | 8/2002 | Crowley et al. |
| 2004/0087936 A1 * | 5/2004 | Stern et al. .................... 606/41 |
| 2004/0254622 A1 | 12/2004 | Shadduck |

FOREIGN PATENT DOCUMENTS

EP    1402837    3/2004

* cited by examiner

*Primary Examiner*—Michael Peffley

(57) ABSTRACT

A medical-treatment electrode assembly includes at least three spaced-apart electrodes contactable with patient tissue and includes at least three leads electrically connected one each to a corresponding one of the electrodes. The leads are electrically connectable to a medical radio-frequency (RF) generator.

18 Claims, 3 Drawing Sheets

MEDICAL-TREATMENT ELECTRODE ASSEMBLY HAVING TREATMENT-MONITORING APPLICATION

FIELD OF THE INVENTION

The present invention is related generally to medical systems, and more particularly to a medical-treatment electrode assembly having treatment-monitoring application.

BACKGROUND OF THE INVENTION

A medical-treatment electrode assembly is known wherein a tube having two electrodes is inserted into a patient's esophagus, wherein the two electrodes are electrically connected to a medical radio-frequency (RF) generator, and wherein the two electrodes are brought into contact with esophageal tissue to treat gastro-esophageal reflux disease. In one procedure, treatment monitoring includes monitoring impedance to current flow at an electrode.

Still, scientists and engineers continue to seek improved medical-treatment electrode assemblies.

SUMMARY

A first expression of a first embodiment of a medical-treatment electrode assembly of the invention includes spaced-apart first, second, and third medical-treatment electrodes and first, second, and third leads. The first, second, and third medical-treatment electrodes each have a contact area contactable with patient tissue. The second medical-treatment electrode is located between the first and third medical-treatment electrodes and is positioned closer to the first medical-treatment electrode than to the third medical-treatment electrode. The contact area of the second medical-treatment electrode is smaller than the contact area of the first medical-treatment electrode. The first lead is electrically connected to the first medical-treatment electrode and is electrically connectable to a first terminal of a medical radio-frequency (RF) generator. The second lead is electrically connected to the second medical-treatment electrode and is electrically connectable to the first terminal. The third lead is electrically connected to the third medical-treatment electrode and is electrically connectable to a second terminal of the medical radio-frequency (RF) generator.

A first expression of a second embodiment of a medical-treatment electrode assembly of the invention includes first, a plurality of second, and a third medical-treatment electrode and a first, a plurality of second, and a third lead. The first, the plurality of second, and the third medical-treatment electrodes are spaced apart from each other and each have a contact area contactable with patient tissue. The plurality of second medical-treatment electrodes is located between the first and third medical-treatment electrodes and is positioned closer to the first medical-treatment electrode than to the third medical-treatment electrode. The contact area of each of the plurality of second medical-treatment electrodes is smaller than the contact area of the third medical-treatment electrode. The first lead is electrically connected to the first medical-treatment electrode and is electrically connectable to a first terminal of a medical radio-frequency (RF) generator. The plurality of second leads is electrically connected one each to a corresponding one of the plurality of second medical-treatment electrodes and is electrically connectable to the first terminal. The third lead is electrically connected to the third medical-treatment electrode and is electrically connectable to a second terminal of the medical radio-frequency (RF) generator.

A first expression of a third embodiment of a medical-treatment electrode assembly of the invention includes a first, a plurality of second, a third, and a plurality of fourth medical-treatment electrodes and a first, a plurality of second, a third, and a plurality of fourth leads. The first, the plurality of second, the third, and the plurality of fourth medical-treatment electrodes are spaced apart from each other and each have a contact area contactable with patient tissue. The plurality of second medical-treatment electrodes is located between the first and the plurality of fourth medical-treatment electrodes and is positioned closer to the first medical-treatment electrode than to the plurality of fourth medical-treatment electrodes. The plurality of fourth medical-treatment electrodes is located between the third and the plurality of second medical-treatment electrodes and is positioned closer to the third medical-treatment electrode than to the plurality of second medical-treatment electrodes. The first lead is electrically connected to the first medical-treatment electrode and is electrically connectable to a first terminal of a medical radio-frequency (RF) generator. The plurality of second leads is electrically connected one each to a corresponding one of the plurality of second medical-treatment electrodes and is electrically connectable to the first terminal. The third lead is electrically connected to the third medical-treatment electrode and is electrically connectable to a second terminal of the medical radio-frequency (RF) generator. The plurality of fourth leads is electrically connected one each to a corresponding one of the plurality of fourth medical-treatment electrodes and is electrically connectable to the second terminal.

Several benefits and advantages are obtained from one or more of the expressions of embodiments of the invention. In one application of the first expression of the first embodiment, by measuring the current in a portion of the second lead which leads only to the second medical-treatment electrode, improved monitoring of tissue treatment is obtained as can be appreciated by those skilled in the art. In one application of the first expression of the second and/or third embodiments, by measuring the separate currents in each of the plurality of the second medical-treatment electrodes, improved monitoring of tissue treatment is obtained as can be appreciated by the artisan.

DETAILED DESCRIPTION

Before explaining several embodiments of the present invention in detail, it should be noted that each embodiment is not limited in its application or use to the details of construction and arrangement of parts and steps illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is further understood that any one or more of the following-described embodiments, expressions of embodiments, examples, etc. can be combined with any one or more of the other following-described embodiments, expressions of embodiments, examples, etc.

Figure 1:
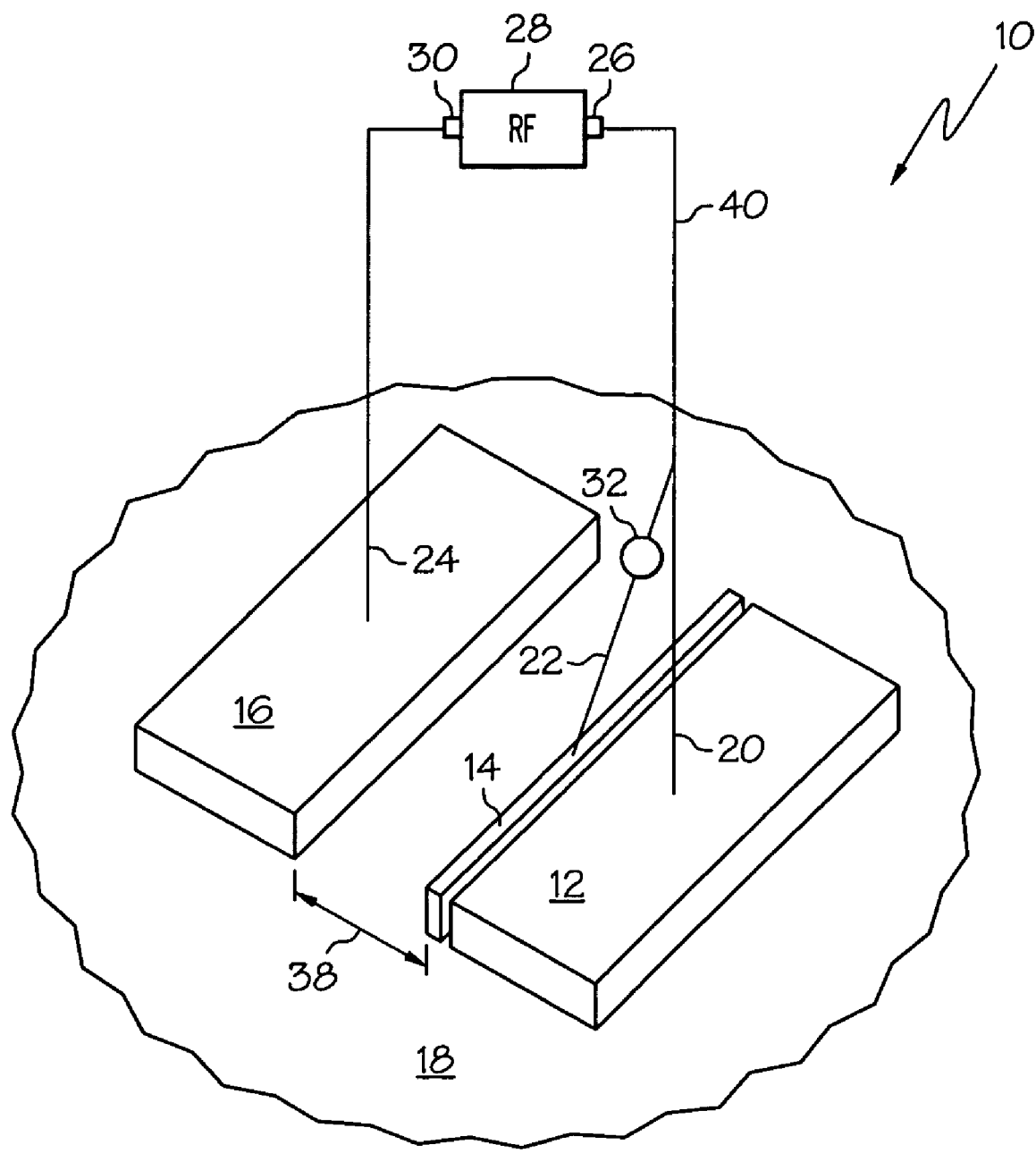
FIG. 1 is a schematic, perspective view of a first embodiment of a medical-treatment electrode assembly of the invention.

A first embodiment of a medical-treatment electrode assembly 10 of the invention is shown in FIG. 1. A first expression of the embodiment of FIG. 1 is for a medical-treatment electrode assembly 10 including spaced-apart first, second, and third medical-treatment electrodes 12, 14 and 16 each having a contact area contactable with patient tissue 18. The second medical-treatment electrode 14 is disposed between the first and third medical-treatment electrodes 12 and 16 and is disposed closer to the first medical-treatment electrode 12 than to the third medical-treatment electrode 16. The contact area of the second medical-treatment electrode 14 is smaller than the contact area of the first medical-treatment electrode 12. The medical-treatment electrode assembly 10 also includes first, second, and third leads 20, 22 and 24. The first lead 20 is electrically connected to the first medical-treatment electrode 12 and is electrically connectable to a first terminal 26 of a medical radio-frequency (RF) generator 28. The second lead 22 is electrically connected to the second medical-treatment electrode 14 and is electrically connectable to the first terminal 26. The third lead 24 is electrically connected to the third medical-treatment electrode 16 and is electrically connectable to a second terminal 30 of the medical radio-frequency (RF) generator 28. It is noted that a voltage differential exists across the first and second terminals 26 and 30 when the medical radio-frequency (RF) generator 28 is operating.

In one deployment of the first expression of the embodiment of FIG. 1, no electrode is disposed between the first and second medical-treatment electrodes 12 and 14.

In one extension of the first expression of the embodiment of FIG. 1, the medical-treatment electrode assembly 10 also includes a current meter 32. The current meter 32 is operatively connected to determine a current, in a portion of the second lead 22 which leads only to the second medical-treatment electrode 14, when current is flowing in the patient tissue 18 between the second and third medical-treatment electrodes 14 and 16 and between the first and third medical-treatment electrodes 12 and 16.

In one arrangement of the first expression of the embodiment of FIG. 1, the contact area of the first, second, and third medical-treatment electrodes 12, 14 and 16 each has a substantially rectangular shape including a length and a width. The contact area in FIG. 1 is the area under the first, second, and third medical-treatment electrodes 12, 14 and 16. In one variation, the first, second and third medical treatment electrodes 12, 14 and 16 are substantially parallel and width-wise aligned. By "width-wise aligned" is meant, with reference to the three electrodes seen in FIG. 1, that the electrodes have substantially the same length, that the left width-wise edge of any one electrode is aligned with the left width-wise edge of each of the other two electrodes and that the right width-wise edge of any one electrode is aligned with the right width-wise edge of each of the other two electrodes.

In one example of this arrangement, the sum of the widths of the first medical-treatment electrode 12 and all medical-treatment electrodes (e.g., electrode 14 in FIG. 1) disposed between the first and third medical-treatment electrodes 12 and 16 is substantially equal to the width of the third medical-treatment electrode 16. This means that, in this example, the distance between the first and second medical-treatment electrodes 12 and 14 is quite small compared to the width of the third medical-treatment electrode 16.

In the same or a different example, the width of the first medical-treatment electrode 12 is at least twenty-five times greater than the width of the second medical-treatment electrode 14. In one variation, the distance (i.e., the gap 38) between the second and the third medical-treatment electrodes 14 and 16 is at least twenty-five times greater than the width of the second medical-treatment electrode 14.

In one enablement of the first expression of the embodiment of FIG. 1, the first, second, and third medical-treatment electrodes 12, 14 and 16 are insertable into the esophagus of a patient (only a portion of patient tissue 18 of which is shown in FIG. 1). In one illustration, the third electrode 16 has a length of substantially twenty millimeters and a width of substantially five millimeters, and the distance (i.e., the gap 38) between the second medical-treatment electrode 14 and the third medical-treatment electrode 16 is substantially two millimeters. In this illustration, the first medical-treatment electrode 12 has a length of substantially twenty millimeters and a width of substantially five millimeters, the second medical-treatment electrode 14 has a length of substantially twenty millimeters, and a width of substantially one-half millimeter, wherein the distance between the first and second medical-treatment electrodes 12 and 14 is substantially one-half millimeter. The thickness of each of the medical-treatment electrodes 12, 14 and 16 is substantially two millimeters.

In one construction of the first expression of the embodiment of FIG. 1, the medical-treatment electrodes 12, 14 and 16 are supported on the outside of a transparent tube (not shown) which is insertable into a patient. In one variation, the medical-treatment electrodes 12, 14 and 16 are bonded to a transparent substrate (not shown) which is attached to the outside surface of the transparent tube. A video camera of an endoscope (not shown) inserted into the tube can, during medical treatment, visually monitor patient tissue in the gap 38 between the second and third medical-treatment electrodes 14 and 16.

A first method for medically treating patient tissue 18 using the medical-treatment electrode assembly 10 includes steps a) through d). Step a) includes contacting the patient tissue 18 with the first, second, and third medical-treatment electrodes 12, 14 and 16. Step b) includes applying a same voltage differential between the first and third medical-treatment electrodes 12 and 16 and between the second and the third medical-treatment electrodes 14 and 16 using the medical radio-frequency (RF) generator 28. Step c) includes monitoring a current in a portion of the second lead 22 which leads only to the second medical-treatment electrode 14 (such as, without limitation, by using the current meter 22). Step d) includes ceasing applying the voltage differential based at least on step c).

In one modification of the first expression of the embodiment of FIG. 1, when the first, second, and third medical-treatment electrodes 12, 14 and 16 are in contact with the patient tissue 18, the patient tissue 18 between the second and third medical-treatment electrodes 14 and 16 is directly and/or indirectly visually observable.

A second method for medically treating patient tissue 18 using the medical-treatment electrode assembly 10, as modified for visual observing between the second and third medical-treatment electrodes 14 and 15, includes steps a) through step e). Step a) includes contacting the patient tissue 18 with the first, second, and third medical-treatment electrodes 12, 14 and 16. Step b) includes applying a same voltage differential between the first and third medical-treatment electrodes 12 and 16 and between the second and third medical-treatment electrodes 14 and 16 using the medical radio-frequency (RF) generator 28. Step c) includes visually monitoring the patient tissue 18 between the second and third medical-treatment electrodes 14 and 16. Step d) includes monitoring a current in a portion of the second lead 22 which leads only to the second medical-treatment electrode 14. Step e) includes ceasing applying the voltage differential based at least on steps c) and d).

A second expression of the embodiment of FIG. 1 is for a medical-treatment electrode assembly 10 including spaced-apart first, second, and third medical-treatment electrodes 12, 14 and 16 and including first, second, and third leads 20, 22 and 24. The first, second, and third medical-treatment electrodes 12, 14 and 16 each have a contact area contactable with patient tissue 18. The second medical-treatment electrode 14 is disposed between the first and third medical-treatment electrodes 12 and 16 and is disposed closer to the first medical-treatment electrode 12 than to the third medical-treatment electrode 16. The contact area of the second medical-treatment electrode 14 is smaller than the contact area of the first medical-treatment electrode 12. The first lead 20 is electrically connected to the first medical-treatment electrode 12 and is electrically connected to a first terminal 26 of a medical radio-frequency (RF) generator 28. The second lead 22 is electrically connected to the second medical-treatment electrode 14 and is electrically connected to the first terminal 26. The third lead is electrically connected to the third medical-treatment electrode 16 and is electrically connected to a second terminal 30 of the medical radio-frequency (RF) generator 28. It is noted that the first and second leads 20 and 22 are described as being electrically connected to the same terminal if they have the same electrical potential with respect to the third lead 24. The contact area of the first, second, and third medical-treatment electrodes 12, 14 and 16 each has a substantially rectangular shape with a length and a width, and the first, second and third medical treatment electrodes 12, 14 and 16 are substantially parallel and width-wise aligned.

It is noted that the extensions, arrangements, examples, etc. of the first expression of the embodiment of FIG. 1 are equally applicable to the second expression of the embodiment of FIG. 1.

Figure 2:
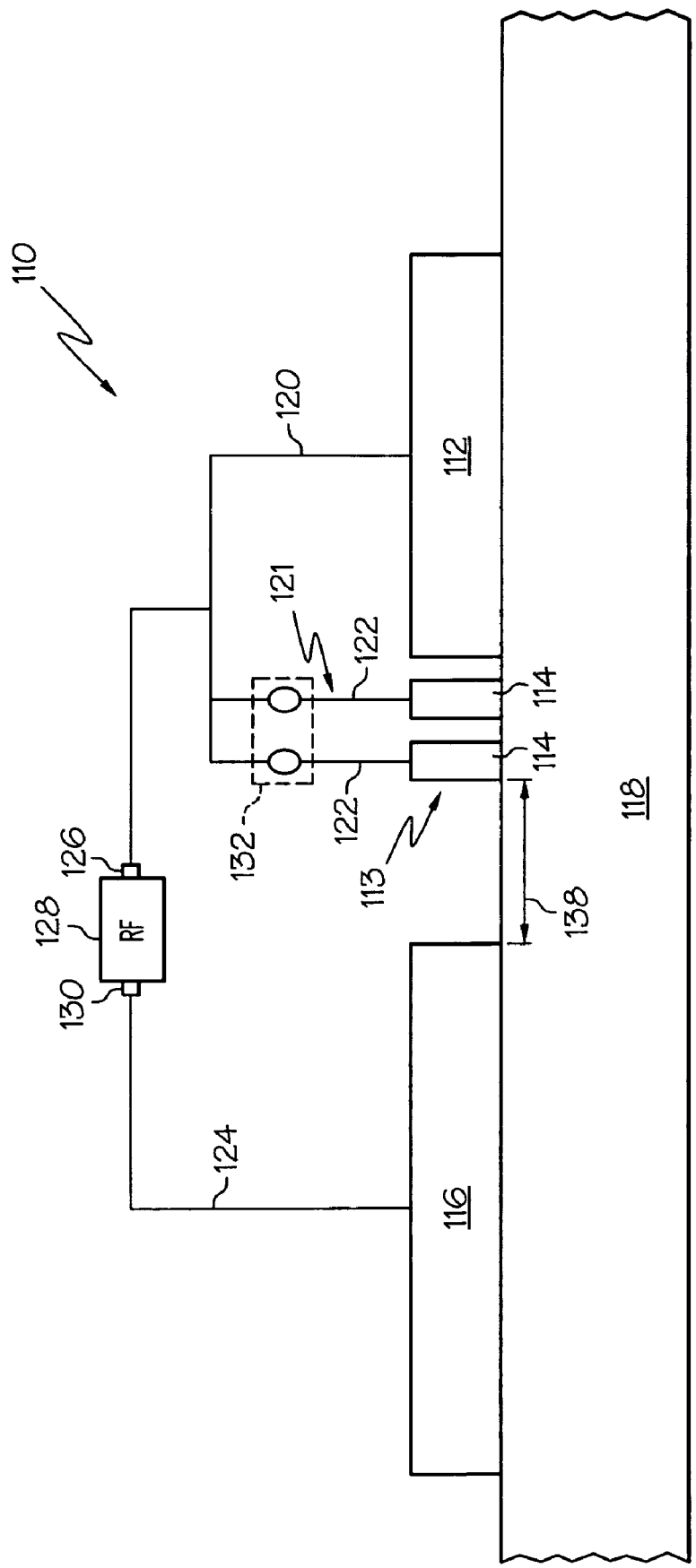
FIG. 2 is a schematic, end elevational view of a second embodiment of a medical-treatment electrode assembly of the invention.

A second embodiment of a medical-treatment electrode assembly 110 of the invention is shown in FIG. 2. A first expression of the embodiment of FIG. 2 is for a medical-treatment electrode assembly 110 including a first 112, a plurality 113 of second 114, and a third 116 medical-treatment electrode spaced apart from each other and each having a contact area contactable with patient tissue 118. The plurality 113 of second medical-treatment electrodes 114 is disposed between the first and third medical-treatment electrodes 112 and 116 and is disposed closer to the first medical-treatment electrode 112 than to the third medical-treatment electrode 116. The contact area of each of the plurality 113 of second medical-treatment electrodes 114 is smaller than the contact area of the third medical-treatment electrode 116. The medical-treatment electrode assembly 110 also includes a first 120, a plurality 121 of second 122, and a third 124 lead. The first lead 120 is electrically connected to the first medical-treatment electrode 112 and is electrically connectable to a first terminal 126 of a medical radio-frequency (RF) generator 128. The plurality 121 of second leads 122 is electrically connected one each to a corresponding one of the plurality 113 of second medical-treatment electrodes 114 and is electrically connectable to the first terminal 126. The third lead 124 is electrically connected to the third medical-treatment electrode 116 and is electrically connectable to a second terminal 130 of the medical radio-frequency (RF) generator 128. The contact area of the first 112, each of the plurality 113 of second 114, and the third 116 medical-treatment electrodes each has a substantially rectangular shape including a length and a width. The first 112, each of the plurality 113 of second 114, and the third 116 medical treatment electrodes are substantially parallel and width-wise aligned. It is noted that a voltage differential exists across the first and second terminals 126 and 130 when the medical radio-frequency (RF) generator 128 is operating.

It is noted that describing the plurality 113 of second medical-treatment electrodes 114 as being closer to the first medical-treatment electrode 112 than to the third medical-treatment electrode 115 means that the closest one of the second electrodes 114 to the first electrode 112 is closer to the first electrode 112 than the closest one of the second electrodes 114 to the third electrode 116 is close to the third electrode 116.

In one deployment of the first expression of the embodiment of FIG. 2, no electrode is disposed between the first 112 and the plurality 113 of second 114 medical-treatment electrodes.

In one extension of the first expression of the embodiment of FIG. 2, the medical-treatment electrode assembly 110 also includes a current meter 132. The current meter 132 is operatively connected to determine separate currents, in each of the plurality 113 of second medical-treatment electrodes 114, when current is flowing in the patient tissue 118 between the plurality 113 of second 114 and the third 116 medical-treatment electrodes and between the first 112 and the third 116 medical-treatment electrodes.

In one example of the second expression of the embodiment of FIG. 2, the sum of the widths of the first 112 and the plurality 113 of second 114 medical-treatment electrodes is substantially equal to the width of the third medical-treatment electrode 116.

In the same or a different example, the width of the first medical-treatment electrode 112 is at least twenty-five times greater than the width of any of the plurality 113 of second 114 medical-treatment electrodes. In one variation, the distance between the plurality 113 of second 114 and the third 116 medical-treatment electrodes is at least twenty-five times greater than the width of any of the plurality 113 of second 114 medical-treatment electrodes.

Figure 3:
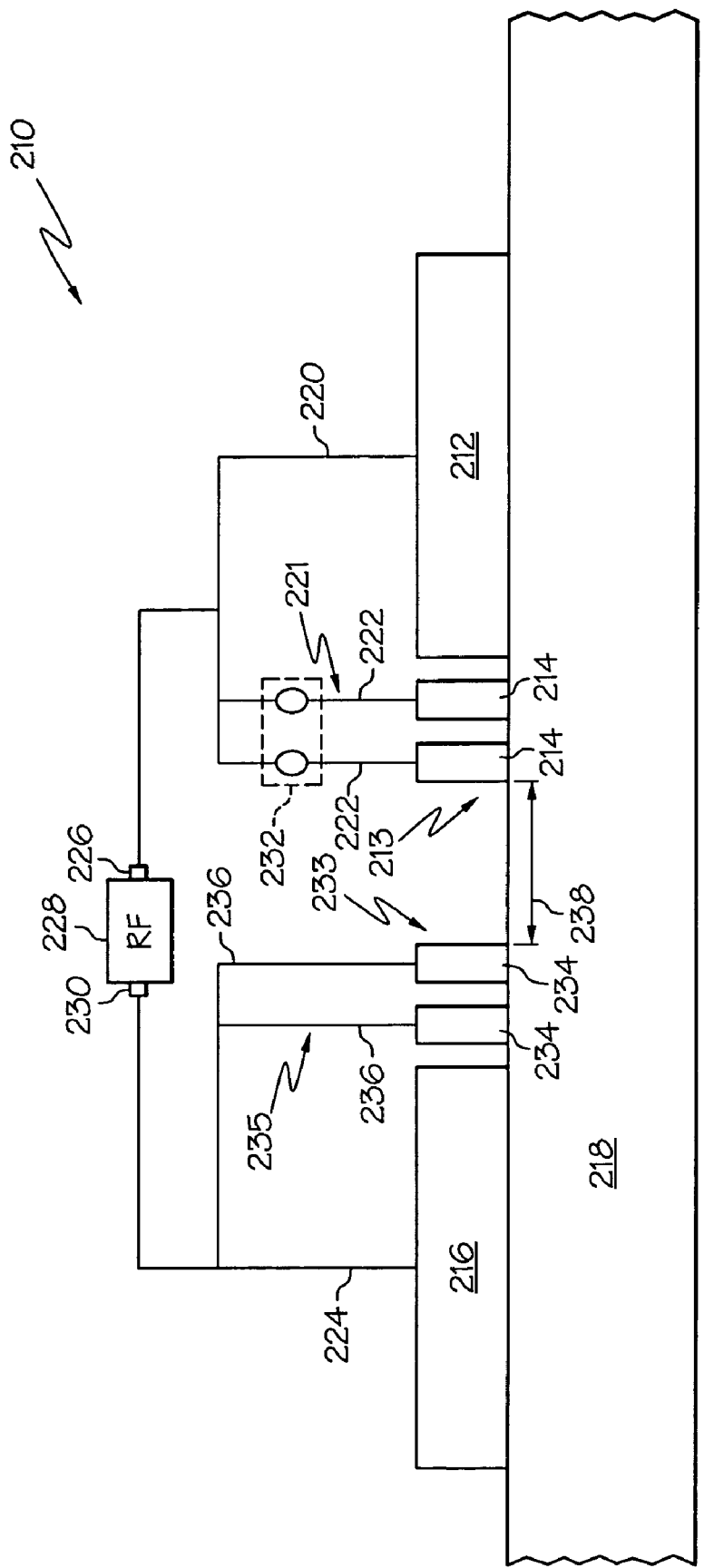
FIG. 3 is a schematic, end elevational view of a third embodiment of a medical-treatment electrode assembly of the invention.

A third embodiment of a medical-treatment electrode assembly 210 of the invention is shown in FIG. 3. A first expression of the embodiment of FIG. 3 is for a medical-treatment electrode assembly 210 including a first 212, a plurality 213 of second 214, a third 216, and a plurality 233 of fourth 234 medical-treatment electrodes spaced apart from each other and each having a contact area contactable with patient tissue 218. The plurality 213 of second medical-treatment electrodes 214 is disposed between the first 212 and the plurality 233 of fourth 244 medical-treatment electrodes and is disposed closer to the first medical-treatment electrode 212 than to the plurality 233 of fourth 234 medical-treatment electrodes. The plurality 233 of fourth 234 medical-treatment electrodes is disposed between the third 216 and the plurality 213 of second 214 medical-treatment electrodes and is disposed closer to the third 216 medical-treatment electrode than to the plurality 213 of second 214 medical-treatment electrodes. The medical-treatment electrode assembly 210 also includes a first 220, a plurality 221 of second 222, a third 224, and a plurality 235 of fourth 236 lead. The first lead 220 is electrically connected to the first medical-treatment electrode 212 and is electrically connectable to a first terminal 226 of a medical radio-frequency (RF) generator 228. The plurality 221 of second leads 222 is electrically connected one each to a corresponding one of the plurality 213 of second medical-treatment electrodes 214 and is electrically connectable to the first terminal 226. The third lead 224 is electrically connected to the third medical-treatment electrode 216 and is electrically connectable to a second terminal 230 of the medical radio-frequency (RF) generator 228. The plurality 235 of fourth 236 leads is electrically connected one each to a corresponding one of the plurality 233 of fourth 234 medical-treatment electrodes and is electrically connectable to the second terminal 230. It is noted that a voltage differential exists across the first and second terminals 226 and 230 when the medical radio-frequency (RF) generator 228 is operating.

In one deployment of the first expression of the embodiment of FIG. 3, no electrode is disposed between the first 112 and the plurality 113 of second 114 medical-treatment electrodes and no electrode is disposed between the third 116 and the plurality 235 of fourth 236 medical-treatment electrodes.

In one extension of the first expression of the embodiment of FIG. 3, the medical-treatment electrode assembly 210 also includes a current meter 232. The current meter 232 is operatively connected to determine separate currents, in each of the plurality 213 of second medical-treatment electrodes 214, when current is flowing in the patient tissue 218 between the plurality 213 of second 214 and at least one of the plurality 233 of fourth 234 medical-treatment electrodes.

In one enablement of the first expression of the embodiment of FIG. 3, the distance between the plurality 213 of second 214 and the plurality 233 of fourth 234 medical-treatment electrodes is at least twenty-five times greater than the distance between adjacent electrode pairs of the plurality 213 of second medical-treatment electrodes 214 and is at least twenty-five times greater than the distance between adjacent electrode pairs of the plurality 233 of fourth medical-treatment electrodes 234.

The following paragraphs present a discussion of one implementation of any one or more or all of the expressions of the first, second, and third embodiments of the medical-treatment electrode assembly 110, 210 and 310.

Clinically, it is useful to be able to ablate, in a controlled way, to shallow depths below a tissue surface. In particular, this can be applied to the treatment of Barrett's disease on the inner lining of the esophagus.

The medical-treatment electrode assembly 110, 210 and 310 generates an ablation zone that begins in the gap 38, 138 and 238. The geometry of the electrodes and the gap between them are chosen such that when the surface of the tissue visible in the gap is coagulated, the resulting ablation volume will have a length, width and depth that fall within desired ranges.

With the exception of the region at the very ends of the electrodes, we can well describe the medical treatment by just considering the electrode width dimension, the gap, and the tissue depth. The electrode arrangement results in coagulation beginning at the outer edges of the gap, propagating toward the center until the entire visible surface is coagulated. At this moment, for certain electrode parameters, an approximately semicircular ablation volume profile will exist in the tissue confined to the gap region and reaching a depth that is clinically desirable (0.5 to 1 mm). It should be noted that some of the ablation volume will extend less than a millimeter beyond the gap region just under the tissue surface. A visual cue is provided as feedback that ablation to the desired depth has been achieved, well confined to the gap region.

As tissue is heated, its electrical and thermal properties change. In particular, its electrical conductivity undergoes a significant increase as the temperature is increased above body temperature until a breakpoint in the 70C to 80C range beyond which it drops dramatically. In the vicinity of 100C, phase transition phenomena begin. Thus, as the bulk tissue is heated, its ability to conduct current varies from point to point depending on temperature. This results in a nonlinear evolution of the distribution of current density as the ablation proceeds. In fact, if temperatures are raised high enough, regions of tissue will cease to conduct current. If the entire tissue region in contact with the electrodes should undergo this transition to high impedance, current flow will cease altogether and the system will no longer heat tissue.

If the medical-treatment electrode assembly 10, 110 and 210, with certain electrode parameters, is operated just until the gap is coagulated, virtually no surface tissue is coagulated in contact with the electrodes. Thus, if RF power is maintained and the tissue is thick enough, deeper and deeper pathways for current will be used even as the tissue near the surface in the gap region is ablated to the point of zero conductance. In fact, the apparent bulk tissue impedance measured via the electrodes will change little until much later in the process (if allowed to continue) when significant portions of the electrode width will be in contact with ablated tissue. This would result in ablation volumes with increase depths.

Control of ablation depths is obtainable based on visual and/or non-visual cues of coagulation in the gap. One non-visual cue is directly measuring a tissue property that changes during a firing in a way that correlates to the ablation depth. One choice is to measure tissue impedance. Without the second or plurality of second medical-treatment electrodes, only measurements of bulk impedance are obtainable. The bulk impedance changes very little particularly during the early stages.

The presence of the second or plurality of second medical-treatment electrodes preserves the visual cue in the gap (if desired) while allowing a simple measurement of impedance that is more sensitive to tissue changes in the gap region. The second and or the plurality of second electrodes adjacent to the gap are very narrow in width, are isolated from each other, and are maintained at the same electrical potential during operation. The current flowing through the lead of the second or each or the plurality of second electrodes is individually measurable.

The current pathways available to the second or the closer-to-the-gap ones of the plurality of second electrodes will change more dramatically than those further from the gap as the tissue impedance changes in the gap region. Measuring the impedance seen by the second and each of the plurality of second electrodes by measuring the current that they draw provides a more sensitive means to assess tissue changes, particularly in the gap. In fact, if ablation proceeds to the point of coagulating the tissue surface under the narrow second or closer-to-the-gap ones of the plurality of second electrodes, nearly complete shutdown of current flow to the second or the closer-to-the-gap ones of the plurality of second electrodes would result giving a method for non-visually monitoring the ablation progress.

Provided with a sensitive method for detecting tissue impedance changes, useful correlation between the measured impedance and ablation volume depth can be found. If multiple segments (i.e., the plurality of second and/or fourth medical-treatment electrodes) are made in the electrodes (i.e., ending up with a first and a third and a plurality of second and/or fourth electrodes), measured impedance changes with the segments will propagate outward from the gap 138 and 238 edge in time as the ablation volume grows deeper.

Applicant has performed a finite element analysis of a model of the medical-treatment electrode assembly 10 of FIG. 1. A finite element model of this system demonstrated sensitivity to tissue impedance changes. The model was run with a simulated RF generator input corresponding to an ICC350 operating at 30 Watts. Simulation time was 1.35 seconds. The impedance measured using a portion of the second lead 22 which leads only to the second medical-treatment electrode 14 showed a dramatic change compared to the impedance measured using a portion of the first lead 20 which leads only to the first medical-treatment electrode 12 or compared to the impedance measured using the common portion of the lead 40 which branches into the first and second leads 20 and 22.

Several benefits and advantages are obtained from one or more of the expressions of embodiments of the invention. In one application of the first expression of the first embodiment, by measuring the current in a portion of the second lead which leads only to the second medical-treatment electrode, improved monitoring of tissue treatment is obtained as can be appreciated by those skilled in the art. In one application of the first expression of the second and/or third embodiments, by measuring the separate currents in each of the plurality of the second medical-treatment electrodes, improved monitoring of tissue treatment is obtained as can be appreciated by the artisan.

While the present invention has been illustrated by a description of several embodiments and examples, etc. thereof, it is not the intention of the applicant to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended Claims.

What is claimed is:

1. A medical-treatment electrode assembly comprising:
   a) spaced-apart first, second, and third medical-treatment electrodes each having a contact area contactable with patient tissue, wherein the second medical-treatment electrode is disposed between the first and third medical-treatment electrodes and is disposed closer to the first medical-treatment electrode than to the third medical-treatment electrode, and wherein the contact area of the second medical-treatment electrode is smaller than the contact area of the first medical-treatment electrode; and
   b) first, second, and third leads, wherein the first lead is electrically connected to the first medical-treatment electrode and is electrically connectable to a first terminal of a medical radio-frequency (RF) generator, wherein the second lead is electrically connected to the second medical-treatment electrode and is electrically connectable to the first terminal, wherein the third lead is electrically connected to the third medical-treatment electrode and is electrically connectable to a second terminal of the medical radio-frequency (RF) generator, and wherein the contact area of the first, second, and third medical-treatment electrodes each has a substantially rectangular shape including a length and a width.

2. The medical-treatment electrode assembly of claim 1, wherein the first, second and third medical treatment electrodes are substantially parallel and width-wise aligned, and wherein the sum of the widths of the first and second medical-treatment electrodes is substantially equal to the width of the third medical-treatment electrode.

3. The medical-treatment electrode assembly of claim 2, wherein the width of the first medical-treatment electrode is at least twenty-five times greater than the width of the second medical-treatment electrode.

4. The medical-treatment electrode assembly of claim 3, wherein the distance between the second and the third medical-treatment electrodes is at least twenty-five times greater than the width of the second medical-treatment electrode.

5. The medical-treatment electrode assembly of claim 4, wherein the first, second, and third medical-treatment electrodes are insertable into the esophagus of a patient.

6. The medical-treatment electrode assembly of claim 5, wherein the third electrode has a length of substantially twenty millimeters and a width of substantially five millimeters, and wherein the distance between the second medical-treatment electrode and the third medical-treatment electrode is substantially two millimeters.

7. The medical-treatment electrode assembly of claim 1, wherein, when the first, second, and third medical-treatment electrodes are in contact with the patient tissue, the patient tissue between the second and third medical-treatment electrodes is directly and/or indirectly visually observable.

8. A method for medically treating patient tissue using the medical-treatment electrode assembly of claim 1 comprising the steps of:
   a) contacting the patient tissue with the first, second, and third medical-treatment electrodes;
   b) medically treating the patient tissue when the first, second, and third medical-treatment electrodes are contacting the patient tissue by applying a same voltage differential between the first and third medical-treatment electrodes and between the second and third medical-treatment electrodes using the medical radio-frequency (RF) generator;
   c) monitoring a current in a portion of the second lead which leads only to the second medical-treatment electrode; and
   d) stopping the medically treating of the patient tissue when the first, second, and third medical-treatment electrodes are contacting the patient tissue by ceasing applying the voltage differential based at least on step c).

9. A method for medically treating patient tissue using the medical-treatment electrode assembly of claim 7, comprising the steps of:
   a) contacting the patient tissue with the first, second, and third medical-treatment electrodes;
   b) medically treating the patient tissue when the first, second, and third medical-treatment electrodes are contacting the patient tissue by applying a same voltage differential between the first and third medical-treatment electrodes and between the second and third medical-treatment electrodes using the medical radio-frequency (RF) generator;
   c) visually monitoring the patient tissue between the second and third medical-treatment electrodes;
   d) monitoring a current in a portion of the second lead which leads only to the second medical-treatment electrode; and
   e) stopping the medically treating of the patient tissue when the first, second, and third medical-treatment electrodes are contacting the patient tissue by ceasing applying the voltage differential based at least on steps c) and d).

10. A medical-treatment electrode assembly comprising:
    a) spaced-apart first, second, and third medical-treatment electrodes each having a contact area contactable with patient tissue, wherein the second medical-treatment electrode is disposed between the first and third medical-treatment electrodes and is disposed closer to the first medical-treatment electrode than to the third medical-treatment electrode, and wherein the contact area of the second medical-treatment electrode is smaller than the contact area of the first medical-treatment electrode; and b) first, second, and third leads, wherein the first lead is electrically connected to the first medical-treatment electrode and is electrically connected to a first terminal of a medical radio-frequency (RF) generator, wherein the second lead is electrically connected to the second medical-treatment electrode and is electrically connected to the first terminal, and wherein the third lead is electrically connected to the third medical-treatment electrode and is electrically connected to a second terminal of the medical radio-frequency (RF) generator, wherein the contact area of the first, second, and third medical-treatment electrodes each has a substantially rectangular shape with a length and a width, and wherein the first, second and third medical treatment electrodes are substantially parallel and width-wise aligned.

11. A medical-treatment electrode assembly comprising:
a) a first, a plurality of second, and a third medical-treatment electrode spaced apart from each other and each having a contact area contactable with patient tissue, wherein the plurality of second medical-treatment electrodes is disposed between the first and third medical-treatment electrodes and is disposed closer to the first medical-treatment electrode than to the third medical-treatment electrode, and wherein the contact area of each of the plurality of second medical-treatment electrodes is smaller than the contact area of the third medical-treatment electrode; and
b) a first, a plurality of second, and a third lead, wherein the first lead is electrically connected to the first medical-treatment electrode and is electrically connectable to a first terminal of a medical radio-frequency (RF) generator, wherein the plurality of second leads is electrically connected one each to a corresponding one of the plurality of second medical-treatment electrodes and is electrically connectable to the first terminal, and wherein the third lead is electrically connected to the third medical-treatment electrode and is electrically connectable to a second terminal of the medical radio-frequency (RF) generator, wherein the contact area of the first, each of the plurality of second, and the third medical-treatment electrodes each has a substantially rectangular shape including a length and a width, and wherein the first, each of the plurality of second and the third medical treatment electrodes are substantially parallel and width-wise aligned.

12. The medical-treatment electrode assembly of claim 11, also including a current meter operatively connected to determine separate currents, in each of the plurality of second medical-treatment electrodes, when current is flowing in the patient tissue between the plurality of second medical-treatment electrodes and the third medical-treatment electrode and between the first and third medical-treatment electrodes.

13. The medical-treatment electrode assembly of claim 11, wherein the sum of the widths the first and the plurality of second medical-treatment electrodes is substantially equal to the width of the third medical-treatment electrode.

14. The medical-treatment electrode assembly of claim 13, wherein the width of the first medical-treatment electrode is at least twenty-five times greater than the width of any of the plurality of second medical-treatment electrodes.

15. The medical-treatment electrode assembly of claim 14, wherein the distance between the plurality of second medical-treatment electrodes and the third medical-treatment electrodes is at least twenty-five times greater than the width of any of the second medical-treatment electrodes.

16. A medical-treatment electrode assembly comprising:
a) a first, a plurality of second, a third, and a plurality of fourth medical-treatment electrodes spaced apart from each other and each having a contact area contactable with patient tissue, wherein the plurality of second medical-treatment electrodes is disposed between the first and the plurality of fourth medical-treatment electrodes and is disposed closer to the first medical-treatment electrode than to the plurality of fourth medical-treatment electrodes, and wherein the plurality of fourth medical-treatment electrodes is disposed between the third and the plurality of second medical-treatment electrodes and is disposed closer to the third medical-treatment electrode than to the plurality of second medical-treatment electrodes; and
b) a first, a plurality of second, a third, and a plurality of fourth leads, wherein the first lead is electrically connected to the first medical-treatment electrode and is electrically connectable to a first terminal of a medical radio-frequency (RF) generator, wherein the plurality of second leads is electrically connected one each to a corresponding one of the plurality of second medical-treatment electrodes and is electrically connectable to the first terminal, wherein the third lead is electrically connected to the third medical-treatment electrode and is electrically connectable to a second terminal of the medical radio-frequency (RF) generator, and wherein the plurality of fourth leads is electrically connected one each to a corresponding one of the plurality of fourth medical-treatment electrodes and is electrically connectable to the second terminal.

17. The medical-treatment electrode assembly of claim 16, also including a current meter operatively connected to determine separate currents, in each of the plurality of second medical-treatment electrodes, when the current is flowing in the patient tissue between the plurality of second medical-treatment electrodes and the at least one of the plurality of fourth medical-treatment electrode.

18. The medical-treatment electrode assembly of claim 16, wherein the distance between the plurality of second and the plurality of fourth medical-treatment electrodes is at least twenty-five times greater than the distance between adjacent electrode pairs of the plurality of second medical-treatment electrodes and is at least twenty-five times greater than the distance between adjacent electrode pairs of the plurality of fourth medical-treatment electrodes.

* * * * *